(12) United States Patent
Nakao

(10) Patent No.: US 7,270,663 B2
(45) Date of Patent: Sep. 18, 2007

(54) MEDICAL SNARE LOOP WITH INDENTATIONS FOR CHANGING EFFECTIVE SIZE OF LOOP AND ASSOCIATED METHOD

(75) Inventor: Naomi L. Nakao, New York, NY (US)

(73) Assignee: Granit Medical Innovations, LLC, New York, NY (US)

( * ) Notice: Subject to any disclaimer, the term of this patent is extended or adjusted under 35 U.S.C. 154(b) by 60 days.

(21) Appl. No.: 10/687,281

(22) Filed: Oct. 16, 2003

(65) Prior Publication Data

US 2005/0085808 A1 Apr. 21, 2005

(51) Int. Cl.
- *A61B 18/18* (2006.01)
- *A61B 17/24* (2006.01)
- *A61B 17/26* (2006.01)

(52) U.S. Cl. .......................... 606/47; 606/113
(58) Field of Classification Search ............ 606/41–49, 606/110–113, 114, 127; 607/96, 98, 99, 607/113, 116; 604/20, 22, 19
See application file for complete search history.

(56) References Cited

U.S. PATENT DOCUMENTS

| | | | |
|---|---|---|---|
| 4,202,338 A | 5/1980 | Bitrolf | |
| 4,256,113 A | 3/1981 | Chamness | |
| 5,190,542 A | 3/1993 | Nakao et al. | |
| 5,201,740 A | 4/1993 | Nakao et al. | |
| 5,207,686 A | 5/1993 | Dolgin | |
| 5,486,182 A | 1/1996 | Nakao et al. | |
| 5,752,961 A * | 5/1998 | Hill | 606/113 |
| 5,759,187 A * | 6/1998 | Nakao et al. | 606/114 |
| 5,782,840 A * | 7/1998 | Nakao | 606/114 |
| 5,788,710 A * | 8/1998 | Bates et al. | 606/127 |
| 6,007,546 A * | 12/1999 | Snow et al. | 606/113 |
| 6,152,922 A | 11/2000 | Ouchi | |
| 6,348,056 B1 * | 2/2002 | Bates et al. | 606/114 |

* cited by examiner

*Primary Examiner*—Matthew DeSanto
(74) *Attorney, Agent, or Firm*—R. Neil Sudol; Henry D. Coleman; William J. Sapone

(57) ABSTRACT

A medical cauterization snare includes a tubular member such as a catheter, a rod or wire disposed at least partially inside the tubular member, and a resilient loop of a first size attached to a distal end of the rod or wire. The loop includes a nose on a side of the loop opposite the wire. The loop further includes two loop sections each extending between the wire and the nose. The loop sections are each formed with a respective notch or dent for enabling a use of the loop in a second size smaller than the first size. Positioning the loop relative to the tubular member so that the notches or dents are disposed at a mouth opening of the tubular member generates this secondary deployment configuration.

31 Claims, 7 Drawing Sheets

MEDICAL SNARE LOOP WITH INDENTATIONS FOR CHANGING EFFECTIVE SIZE OF LOOP AND ASSOCIATED METHOD

BACKGROUND OF THE INVENTION

This invention pertains to a medical instrument. More particularly, this invention pertains to a medical instrument utilizable in endoscopic procedures. This invention also relates to an associated method.

Medical cauterization snares are essentially electrically energizable loops of wire. A cauterization snare is typically inserted in a collapsed configuration through the biopsy channel of an endoscope into a patient. Inside the patient, the cauterization snare is ejected from the endoscope biopsy channel and naturally expands to an opened configuration under the action of its own internal stresses. The snare is then manipulated from outside the patient and placed over a polyp or other tissue mass. The tubular member is then moved in the distal direction to close the loop about the base of the polyp or tissue mass. Then the cauterization loop is withdrawn in the proximal direction into the tubular member to sever the polyp. Electrical current is conducted through the loop provided that the instrument is connected to a voltage source and provided that the loop is in contact with the patient's tissues. Heat is generated in the loop by virtue of the electrical current conduction.

As disclosed in U.S. Pat. Nos. 5,201,740, 5,190,542, 5,486,182, and 5,759,187, a pouch may be attached to the cauterization snare for capturing a polyp or other tissue mass as it is severed from the patient's internal tissues. One advantage of this structure is that several polyps may be collected in succession during the withdrawal of an endoscope from a patient.

A common problem in endoscopic procedures is that polyps come in different sizes. If the snare used to harvest a polyp is too large, it is difficult to encircle the polyp with the cauterization loop. Other tissue structures within the patient obstruct the proper positioning of the snare about the polyp. In addition, upon placement of the snare about the polyp, the snare frequently does not optimally engage the polyp. For instance, only the two lateral sides of the snare might come into contact with the polyp, the far side of the polyp facing away from the endoscope, being spaced from the cauterization loop.

The conventional solution to the problem of different polyp sizes is to use snares of different sizes. However, this approach is cumbersome in that if a larger snare, for example, has been introduced to capture and ressect a large polyp, that snare needs to be first withdrawn from the biopsy channel only to be replaced by a small (mini) snare to capture a smaller polyp. This procedure is time consuming, and adds cost to the procedure because now two instruments instead of one need to be utilized.

OBJECTS OF THE INVENTION

It is a general object of the present invention to provide an improved cauterization snare.

It is a related object of the present invention to provide an improved endoscopic capture pouch, whether used in part as a cauterization snare or simply as a tissue sample collection device.

A more specific object of the present invention is to provide such a snare or capture pouch that may be effectively used regardless of the specimen size.

Yet a further object of the present invention is to provide such a snare or capture pouch that is simple and inexpensive to manufacture.

These and other objects of the present invention will be apparent from the drawings and descriptions herein. Each object of the invention is believed to be attained by at least one embodiment of the invention. However, there is not necessarily any one embodiment that achieves all of the objects of the invention.

SUMMARY OF THE INVENTION

A medical instrument comprises, in accordance with the present invention, a tubular member, an elongate member disposed at least partially inside the tubular member, and a resilient loop of a given size attached to one end of the elongate member. The loop includes a bend on a side of the loop opposite the elongate member. The loop further includes two loop sections each extending between the elongate member and the bend. At least one of the loop sections is formed with a notch or dent for enabling a use of the loop in another size smaller than the given size upon a positioning of the loop by moving the elongate member relative to the tubular member so that the notch or dent is disposed at a mouth opening of the tubular member. Typically the bend in the loop is part of a nose projecting in the distal direction from the distal side of the loop.

Preferably, each of the loop sections is formed with a respective notch or dent for enabling use of the loop in the smaller size upon a positioning of the loop relative to the tubular member so that the notches or dents are disposed at the mouth opening of the tubular member. In a preferred embodiment, the notch or dent of each loop section extends toward the other loop section, while the loop lies in a single plane, with the notches or dents being located in that plane.

The loop of the medical instrument, as well as the elongate member (a wire) may be made of metal and connected to a voltage or current source. In that case the loop functions as a cauterization snare. A pouch may be attached to the cauterization snare for retrieval of severed tissue masses. Alternatively, the loop may be electrically nonconductive or free of any connection to a voltage or current source. In that case, the instrument functions solely as a retrieval basket or capture device.

The notches or dents facilitate the use of a distal end portion of the loop, which is bounded by the notches or dents on the proximal side and the bend or nose projection on the distal side, as an auxiliary loop necessarily having a size smaller than that of the entire loop. The notches or dents have a size and geometry adapted to releasably catch on the mouth rim of the tubular member, thereby preventing the loop from sliding uncontrollably either in an inward or outward direction. This catching facilitates an effective use of the distal end portion of the loop as a separate, auxiliary loop. At the onset of an endoscopic or other procedure using the auxiliary loop, a proximal portion of the main loop is disposed in a collapsed configuration inside the tubular member. Upon encirclement of a target tissue mass by the auxiliary loop, the auxiliary loop is drawn into the tubular member over the "energy hump" presented by the notches or dents.

Pursuant to another feature of the present invention, the notches or dents are disposed at substantially the same first distance from the one end of the elongate member, on the one side, and substantially the same second distance from the bend or nose projection, on the other side. The first distance is approximately 30% to approximately 40% of the sum of the first distance and the second distance. In other words, the notches are disposed 30% to 40% of the way from the proximal end of the loop to the distal end of the loop. This disposition of the notches results in a small, or auxiliary loop that is not too small for the average small polyp and a full loop that is not too large for the average large polyp.

The geometry of the notches or dents is defined in part by the respective subtended angles. Each notch or dent takes a substantially V shape with a pair of linear loop segments connected to one another by an arcuate bight, the segments being preferably disposed at an angle of approximately 80° to approximately 120° relative to one another. More preferably, the segments are disposed at an angle of approximately 90° to approximately 110° relative to one another.

The loop has a relaxed or opened configuration wherein the loop sections are spaced from one another by a pre-established loop width. Each of the notches or dents has a width dimension measured in a direction from the respective loop section towards the other loop section, the width dimension preferably being no larger than approximately fifteen percent of the loop width. More preferably, the width dimension is no larger than approximately ten percent of the loop width.

The small size of the notches or dents, as defined by the subtended angle and the width of the notches relative to the total loop size, is essential for proper functioning of the instrument. If the notches are too flat or narrow, then the ability of the notches to catch the rim of the tube mouth is reduced. If the notches are too pointed or too large, there is a significantly enhanced danger of unintentionally lacerating or severing the target tissue material. If the notches each extend too far towards the opposing loop section, then the notches can meet too early during a loop closure phase of a cauterization procedure (where the loop is electrically conducting) and short circuit the current path. This would happen when the larger loop is used to engulf and subsequently sever a larger polyp. Thus, it is important that when a larger polyp is engulfed (surrounded) by the larger loop, the delicate dents do not interfere in the proper positioning and surrounding of the larger lesion. The dents need to be delicate enough to provide essentially the same action of the large loop as a "dent-less" loop but yet be able to form a second, smaller loop when necessary.

Pursuant to yet another feature of the present invention, each of the loop sections includes a respective bend disposed between the nose projection and the respective notch or dent. These bends are concave towards the inside of the loop and provide the distal side of the open loop with a larger width than the proximal side of the open loop. More particularly, the loop is widest along a line extending from the bend in one of the loop sections to the bend in the other of the loop sections. The bends are located at the same distance from the nose projection so that the loop is provided with an enlarged distal end portion. The bends facilitate a sufficient opening of the entire loop for large polyp retrieval and of the partial loop or auxiliary loop for small polyp retrieval.

A medical method in accordance with the present invention utilizes an instrument including a tubular member, an elongate member disposed at least partially inside the tubular member, and a resilient loop of a given size attached to one end of the elongate member, the loop including a bend (e.g., nose) on a side of the loop opposite the elongate member, the loop further including two loop sections each extending between the elongate member and the bend, at least one of the loop sections being formed with a respective notch or dent. The method includes (a) inserting an endoscope into a patient, the endoscope having a biopsy channel, (b) inserting the instrument through the biopsy channel, the loop being disposed in the tubular member during the inserting of the instrument, (c) after the inserting of the endoscope and the inserting of the instrument, pushing the elongate member to eject the loop at least partially from the tubular member at a distal end of the endoscope, and (d) using the at least partially ejected loop to encircle a first desired tissue mass of a first (larger) size inside the patient, wherein the loop is substantially entirely outside of the tubular member. The method additionally includes (e) using the at least partially ejected loop to encircle a second desired tissue mass of a second size inside the patient, wherein this second size being substantially smaller than the first size. The loop notch or dent is initially disposed at a mouth opening of the tubular member during the using of the loop to encircle the second desired tissue mass.

DETAILED DESCRIPTION OF THE PREFERRED EMBODIMENTS

Figure 1:
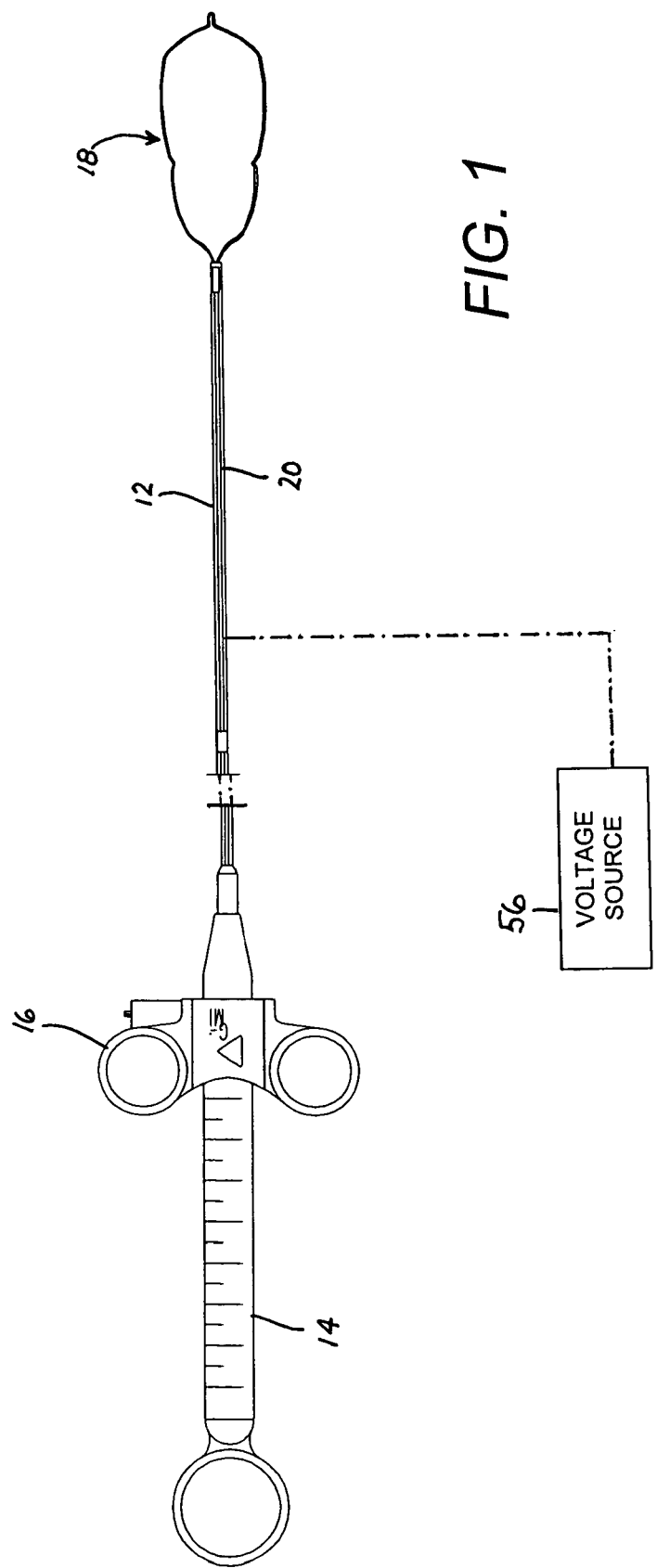
FIG. 1 is a schematic side elevational view of a medical instrument in accordance with the present invention.
Figure 4:
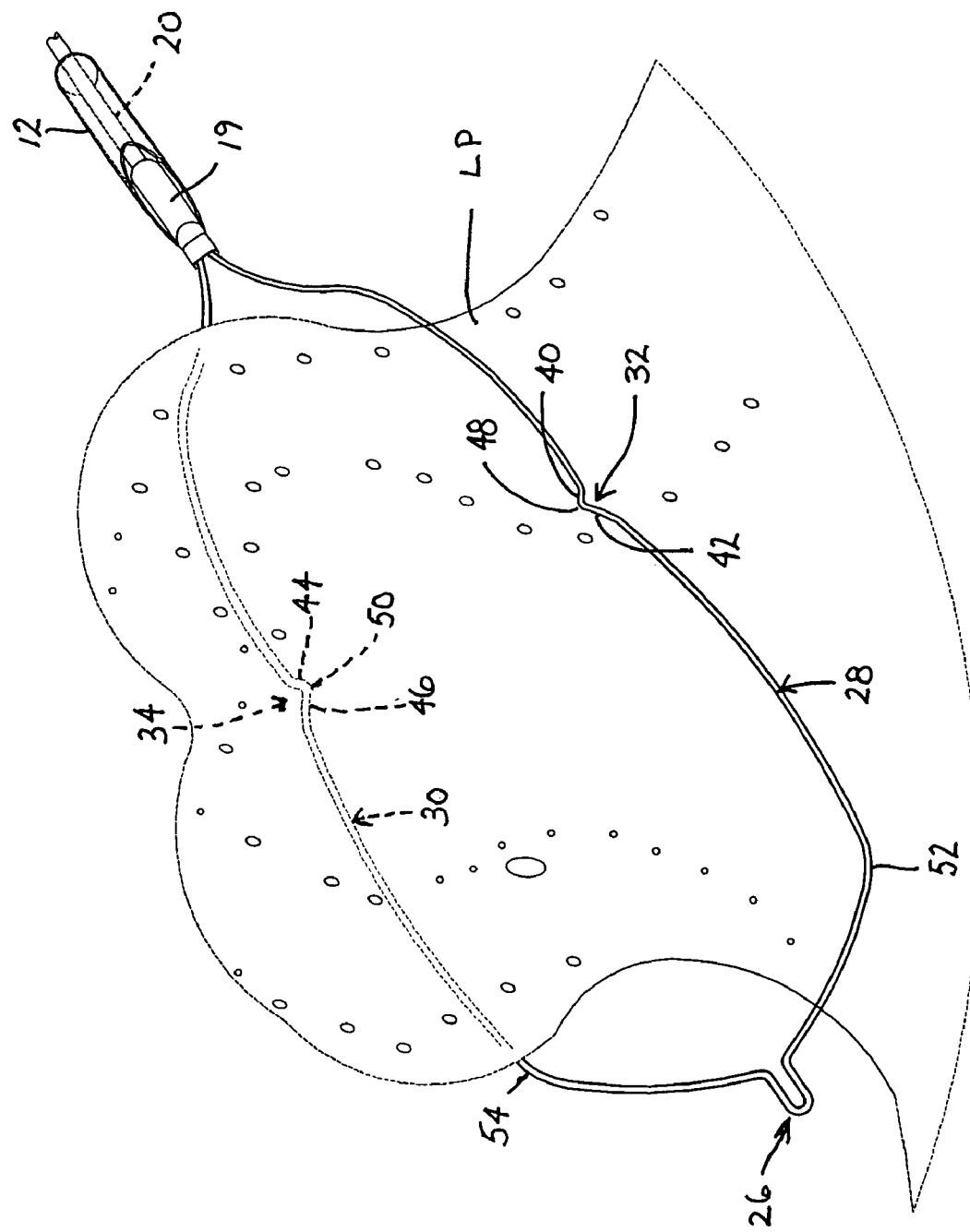
FIG. 4 is a schematic perspective view, showing a step in the use of the cauterization loop of FIGS. 1-3 in the deployment mode of FIG. 2.

As depicted in FIG. 1, an endoscopic cauterization snare instrument comprises an elongate tubular member 12, a handle 14 with a slidable actuator 16, and a resilient loop 18 made of a wire or electrically resistant material as is well known in the art. Tubular member 12 is a catheter attached at its proximal end to handle 14. Loop 18 is attached to a distal end of an elongate rod or wire member 20 extending longitudinally through tubular member 12 to actuator 16. A metal tip element in the form of a sleeve 19 (FIG. 2) is inserted in the distal end of tubular member 12 and is rigidly fastened thereto. Sleeve 19 is a serves as a guide for loop 18 during ejection and retraction procedures. To that end, sleeve 19 is provided at a free end with a segment 21 that is rectangular in cross-section. In FIG. 1, actuator 16 is shown disposed in a most distal position relative to handle or grip 14. In that position of the actuator, loop 18 is in a fully extended and fully opened configuration shown in FIGS. 1 and 2. In that configuration, loop 18 has a size adapted for severing a large polyp LP (FIG. 4).

Figure 2:
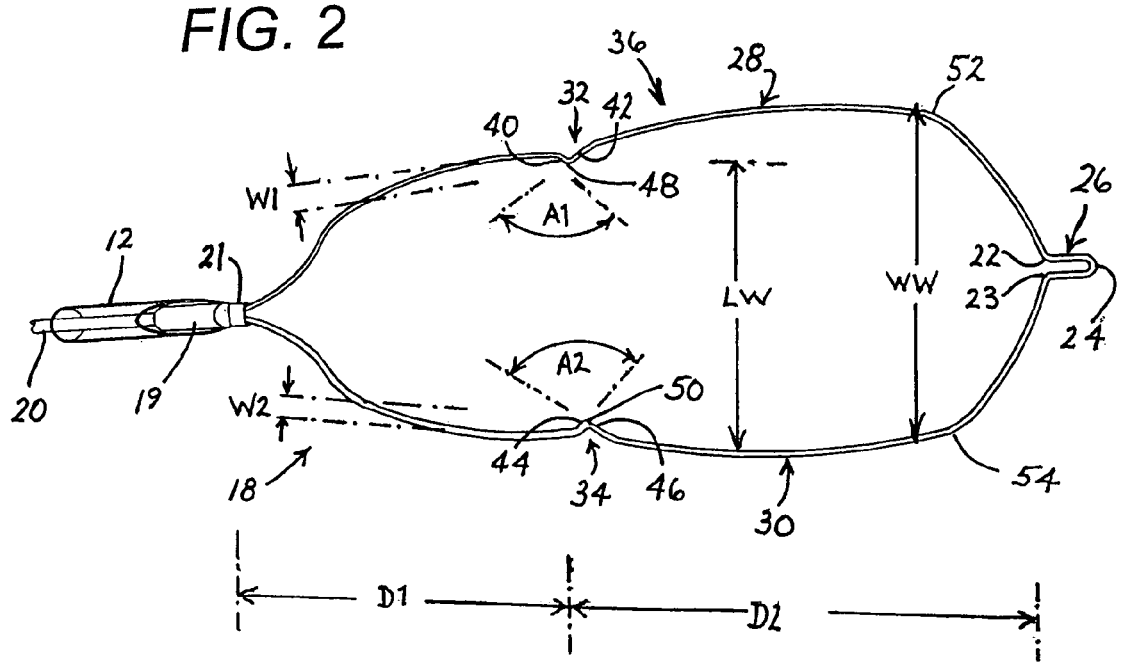
FIG. 2 is a schematic top plan view, on a larger scale, of a cauterization loop shown in FIG. 1, said the cauterization loop in a first deployment mode.

As shown in FIG. 2, loop 18 is formed on a distal side with three bends 22, 23, 24 defining a nose 26 projecting in the distal direction away from tubular member or catheter 12 and rod or wire member 20. Center bend 24 is concave inwardly, while lateral bends 22 and 23 are concave outwardly, that is, in a direction away from the inside of the loop 18. Loop 18 further includes two mirror-image loop sections 28 and 30 each extending between elongate rod or wire member 20 and a respective bend 22 or 23 of nose 26.

Figure 3:
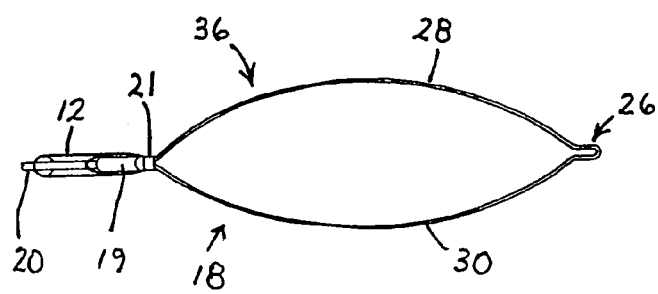
FIG. 3 is a schematic top plan view similar to FIG. 2, showing the cauterization loop of FIGS. 1 and 2 in a second deployment mode.
Figure 5:
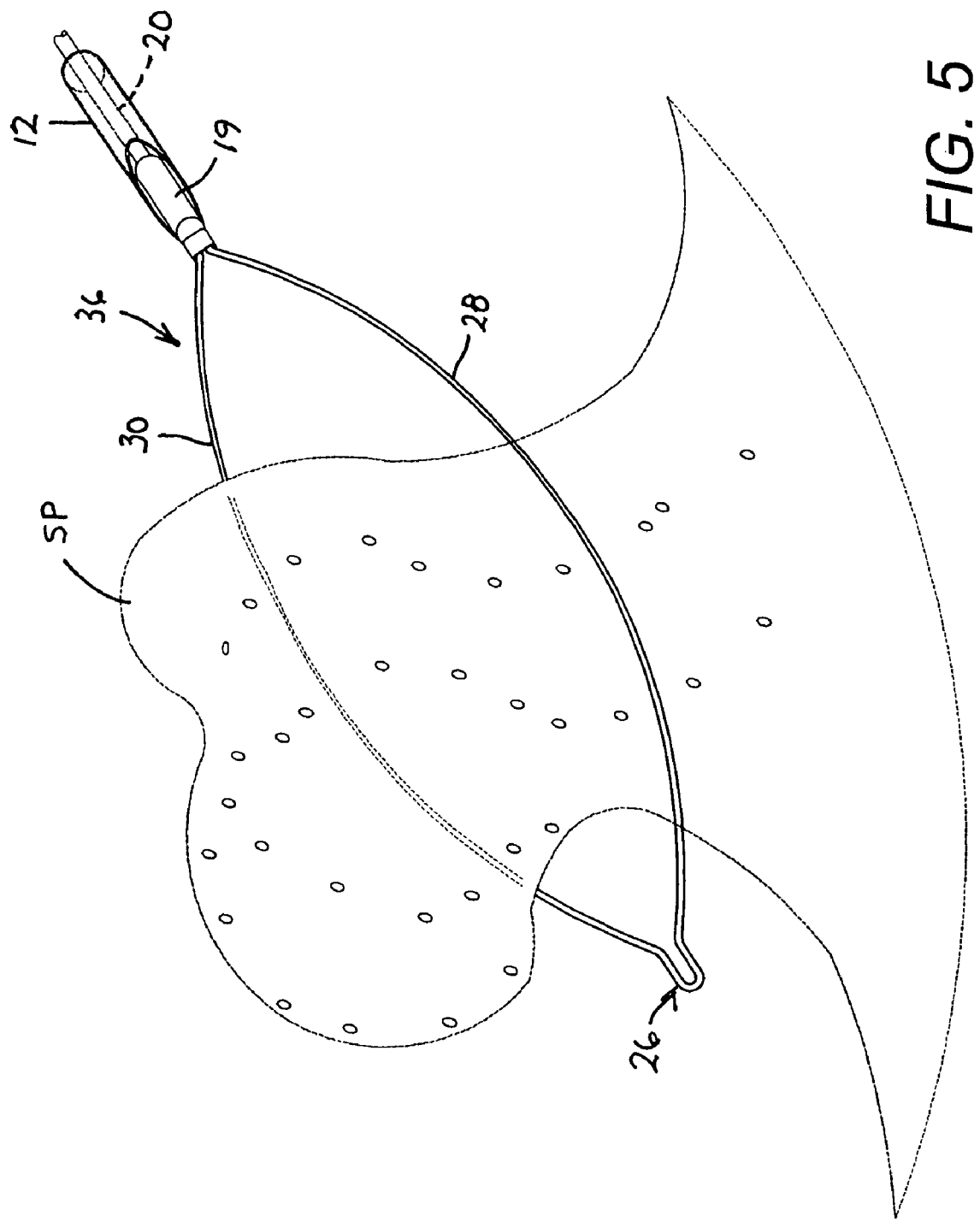
FIG. 5 is a schematic perspective view, showing a step in the use of the cauterization loop of FIGS. 1-3 in the deployment mode of FIG. 3.

Loop sections 28 and 30 are formed with respective V-shaped notches or dents 32 and 34 for enabling a use of the loop in a second, smaller size shown in FIGS. 3 and 5. In this smaller deployment configuration, loop 18 is suitable for the harvesting of a small polyp SP, as depicted in FIG. 5. More specifically, notches or dents 32 and 34 facilitate the use of a distal end portion 36 of loop 16, which is bounded by the notches or dents on the proximal side and nose 26 on the distal side, as a smaller, auxiliary loop. Notches or dents 32 and 34 are so small relative to loop 18 that loop 18 in the fully expanded configuration takes the form of a single oval having a width that is substantially unaffected by the notches or dents so that loop 18 in its fully expanded configuration can be used to sever a polyp substantially larger than any polyp severable by the smaller auxiliary loop formed by distal end portion 36 of loop 18.

Notches or dents 32 and 34 are of a size and geometry to releasably catch on the mouth rim or lip of tubular member 12, thereby preventing loop 18 from sliding uncontrollably either in proximal or distal direction relative to tubular member 12.

Loop 18 generally lies in a single plane. Notches or dents 32 and 34 also lie in that same plane and face through the inside of the loop. In other words, the notch or dent 32, 34 of each loop section 28, 30 extends toward the other loop section 30, 32. Notches or dents 32 and 34 are indentations or dimples, local deformations in loop 18, that do not affect the overall shape of the loop or the directions of loop sections 28 and 30.

Notches or dents 32 and 34 are disposed at substantially the same distance D1 from crimping sleeve 19, which defines the distal end of rod or wire member 20. In addition, notches or dents 32 and 34 are disposed at the same distance D2 from nose 26. Preferably, distance D1 is approximately 30% to approximately 40% of the sum of the distances D1 and D2. This disposition of notches 32 and 34 results in a small or auxiliary loop (FIG. 3) that is not too small for the average small polyp SP (FIG. 5) and a full loop (FIG. 2) that is not too large for the average large polyp LP (FIG. 4).

The geometry of notches or dents 32 and 34 is defined in part by their respective subtended angles A1 and A2. Each notch or dent 32 and 34 takes a substantially V shape with a pair of linear loop segments 40, 42 and 44, 46 connected to one another by a respective arcuate bight 48 and 50. Segments 40 and 42 are preferably disposed at an angle Al of approximately 80° to approximately 120° relative to one another. Likewise, segments 44 and 46 are preferably disposed at an angle A2 of approximately 80° to approximately 120° relative to one another. More preferably, the segments 40, 42 and 44, 46 are disposed at angles A1 and A2 of approximately 90° to approximately 110°.

Loop 18 has a relaxed or opened configuration wherein loop sections 28 and 30 are spaced from one another by a pre-established loop width LW at the locations of notches or detns 32 and 34. Each of the notches or dents 32 and 34 has a width dimension W1, W2 measured generally in a direction from the respective loop section 28 and 30 towards the other loop section 30 and 28, the width dimensions WI and W2 preferably being no larger than approximately fifteen percent of the loop width. More preferably, the width dimensions W1 and W2 are no larger than approximately ten percent of the loop width LW.

The small size of the notches or dents 32 and 34, as defined by the subtended angles A1, A2 and the widths W1, W2 of the notches relative to the total loop width LW, is essential for proper functioning of the instrument. If notches 32 and 34 are too flat or narrow, then their ability to catch the mouth rim or lip of tubular member 12 is reduced. If notches 32 and 34 are too pointed or too large, there is a significantly enhanced danger of unintentionally lacerating or severing polyp LP (FIG. 4). If notches 32 and 34 each extend too far towards the opposing loop section 30 and 28, then the notches can meet too early during a loop closure phase of a cauterization procedure (where the loop is electrically conducting) and short circuit the current path (if the loop is not provided with an insulating layer).

As shown in FIG. 2, in a unstressed or relaxed fully expanded configuration of loop 18 wherein loop sections 28 and 30 are entirely completely outside of tubular member 20, each loop section 28 and 30 includes a respective bend or kink 52 and 54 disposed between nose 26 and the respective notch or dent 32 and 34. These bends or kinks 52 and 54 are concave towards the inside of loop 18 and provide the distal side of the open loop with a larger width WW than the proximal side of the open loop. Bends or kinks 52 and 54 have a radius of curvature that is substantially smaller that the radius of curvature along any other portion of the respective loops sections 28 and 30. Owing to the bowed or oval form of loop 18 in its fully opened deployment configuration (FIG. 2), this widest width WW may be spaced in the proximal direction from a line between bend 52 in loop section 28 and bend 54 in loop section 30. Loop 18 is accordingly provided with an enlarged distal end portion 36. Bends 52 and 54 facilitate a sufficient opening of the entire loop 18 for large polyp (LP) retrieval (FIG. 4) and of the partial loop or auxiliary loop for small polyp (SP) retrieval (FIG. 5). Specifically with respect to the smaller auxiliary configuration illustrated in FIG. 3, the bends 52 and 54 of FIG. 2 optimize or widen the opening of the distal end portion 36 of loop 18 when notches or dents 32 and 34 are withdrawn to and into tubular member 20.

Loop 18 is subject to an electrical current carried via elongate rod or wire member 20 and a connector 21 from a voltage or current source 56 (FIG. 1). Accordingly, the instrument of FIGS. 1-3 may function as a cauterization snare, as illustrated in FIGS. 4 and 5.

Figure 6:
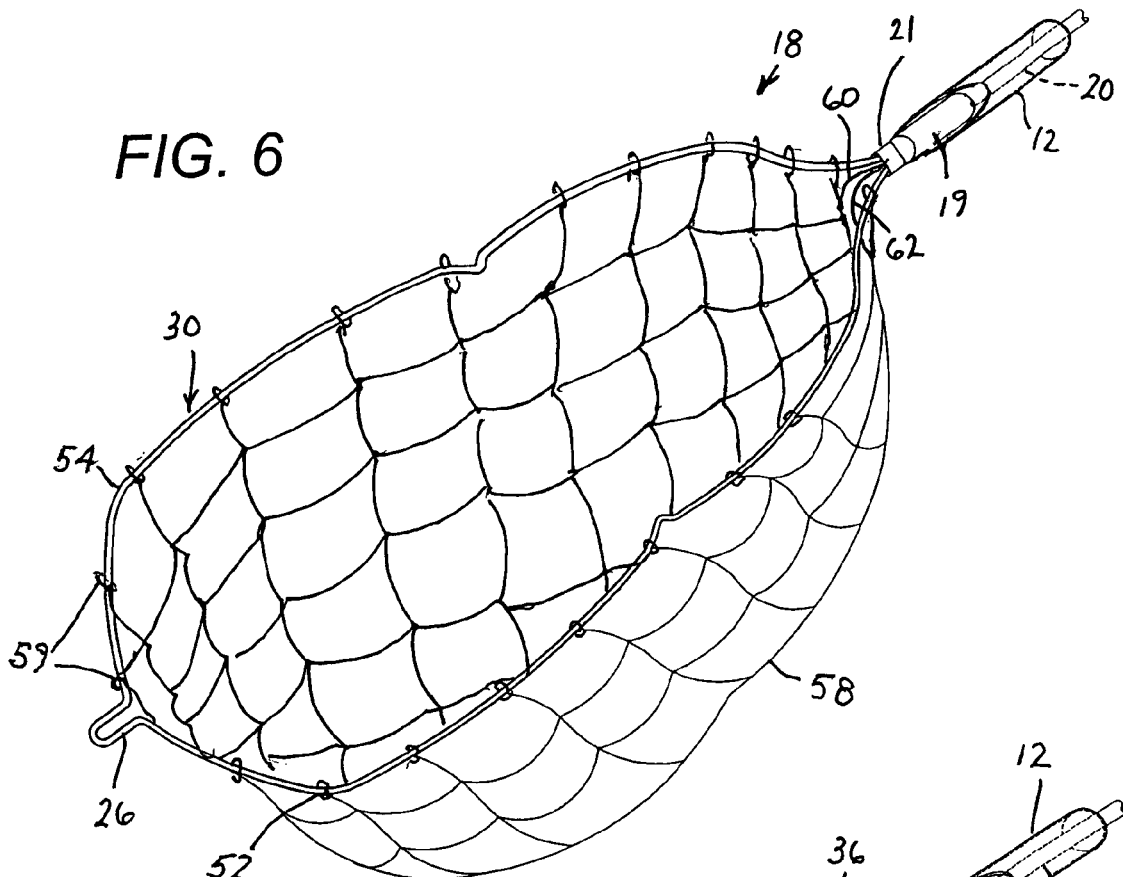
FIG. 6 is a schematic partial perspective view of a medical tissue retrieval or cauterization and retrieval device in accordance with the present invention, showing a loop in a first deployment mode and provided with a pouch to form a capture pocket.

As illustrated in FIG. 6, a flexible basket or pouch 58 made of a netting material may be attached to loop 18 for enabling the severing and retrieval of tissue masses of different sizes. Pouch-holding ringlets 59 are provided at the distal edge of the snare near nose 26, preferably 10 and 11 mm away from the nose. With the instrument of FIGS. 6 and 7, several polyps of different sizes may be severed and captured during the same endoscope deployment procedure, without the necessity for withdrawing the endoscope from the patient upon the severing and capture of each specimen.

Figure 7:
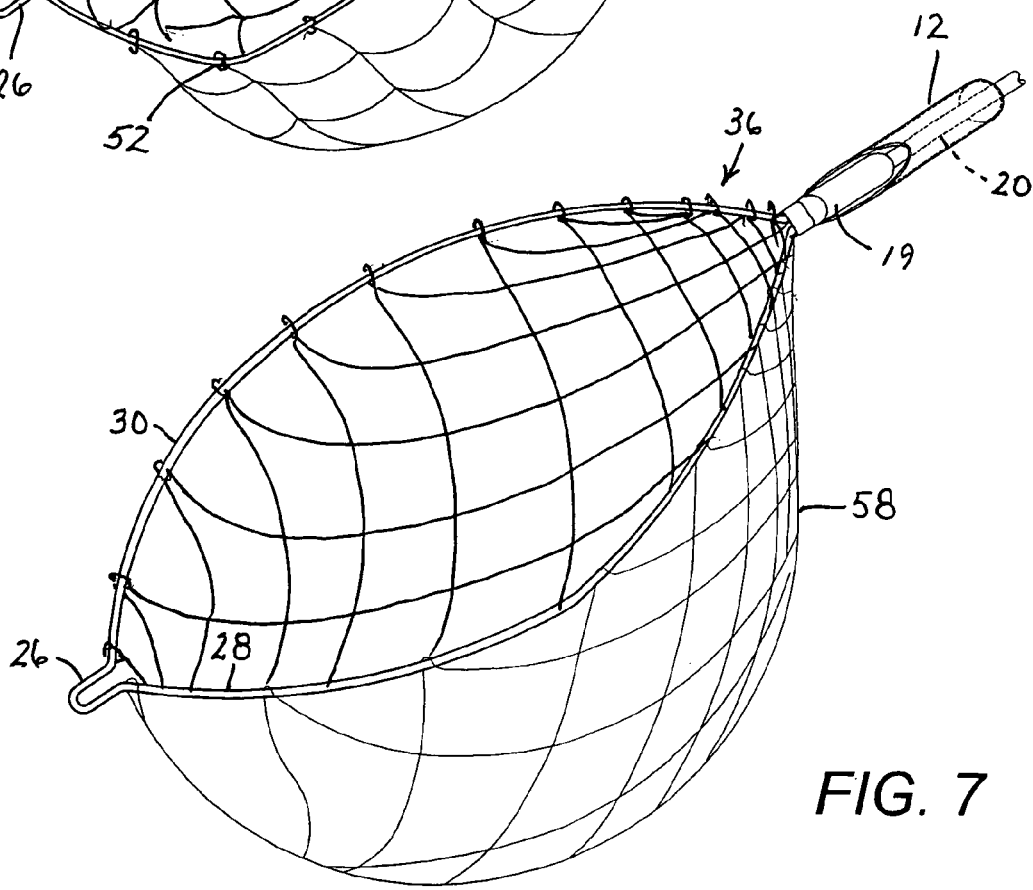
FIG. 7 is a view similar to FIG. 6, showing the loop and pouch in a second, smaller deployment mode.

In an alternative use of the instrument structure shown in FIGS. 6 and 7, loop 18 is electrically non-conductive or free of any connection to a voltage or current source. In that case, the instrument of FIG. 6 functions solely as a specimen retrieval basket or capture device. FIG. 6 shows loop 18 and pouch 58 in a fully extended and fully opened configuration for the retrieval of a large specimen, whereas FIG. 7 shows the loop and the pouch partially drawn into the distal end of tubular member 12 so that the distal end portion of loop 36 forms an auxiliary loop with a portion of pouch 58 depending there from for the retrieval of a small tissue specimen. Again, the instrument of FIGS. 6 and 7 may be used to retrieve multiple tissue masses of different sizes, without having to withdraw the endoscope after each capture.

In a medical method utilizing the instrument of FIGS. 1-3, an endoscope (not shown) is inserted into a patient, the endoscope having a biopsy channel. Tubular member 12 is inserted through the biopsy channel, with loop 18 (and optionally pouch 58) disposed in a collapsed configuration inside the tubular member. After the inserting of the endoscope and the inserting of tubular member 12 into the endoscope biopsy channel, elongate rod or wire member 20 is pushed via actuator 16 in the distal direction to eject loop 18 (and optionally pouch 58) at least partially from tubular member 12 at a distal end of the endsocope. Loop 18 may be completely ejected so as to assume the fully opened configuration of FIG. 2. In that case, handle 14 is manipulated to maneuver loop 18 to encircle a large tissue mass such as polyp LP (FIG. 4). Alternatively, only distal end portion 36 of loop 18 may be disposed outside tubular member 12, as illustrated in FIG. 3. In that case, handle 14 is manipulated to maneuver the auxiliary loop formed by distal end portion 36 to encircle a small tissue mass such as polyp SP (FIG. 5). After the severing and/or capture of a first tissue specimen, a second specimen of the same or different size may be severed and/or captured using the same instrument. There is no need to insert a snare or retrieval device having a different size loop.

At the onset of the endoscopic or other procedure using the auxiliary loop (FIG. 3), a proximal portion of the main loop 18 is disposed in a collapsed configuration inside the tubular member 12. Upon encirclement of a target tissue mass by the auxiliary loop, the auxiliary loop is drawn into the tubular member over an "energy hump" presented by the notches or dents 32 and 34.

As illustrated in FIGS. 6 and 7, the pouch 58 is preferably provided with at least one flexible tensile member or tether 60 and preferably two flexible tensile members 60 and 62 connected to flexible pouch 58 at a proximal end thereof. As disclosed in U.S. Pat. No. 5,759,187, the disclosure of which is hereby incorporated by reference, the flexible tensile members 60 and 62 are also connected to tubular member 12 at a pair of holes (not shown)_formed therein at points spaced from a distal end of the tubular member. Tensile members 60 and 62 extend from pouch 58 into the lumen of tubular member 12. Tensile members 60 and 62 may be segments of a single flexible tensile tether member 64 extending through the holes in tubular member 12. A patch (not shown) may be disposed on an outer surface of tubular member 12 over the holes therein and over a bight portion of tether member 64 which is located outside the tubular member. The patch is a thin film of polymeric material which is heat shrunk tightly over the tubular member 12. The patch ensures that the bight portion of tether member 64 is not snagged on possible protuberances inside the endoscope biopsy channel.

Figure 8:
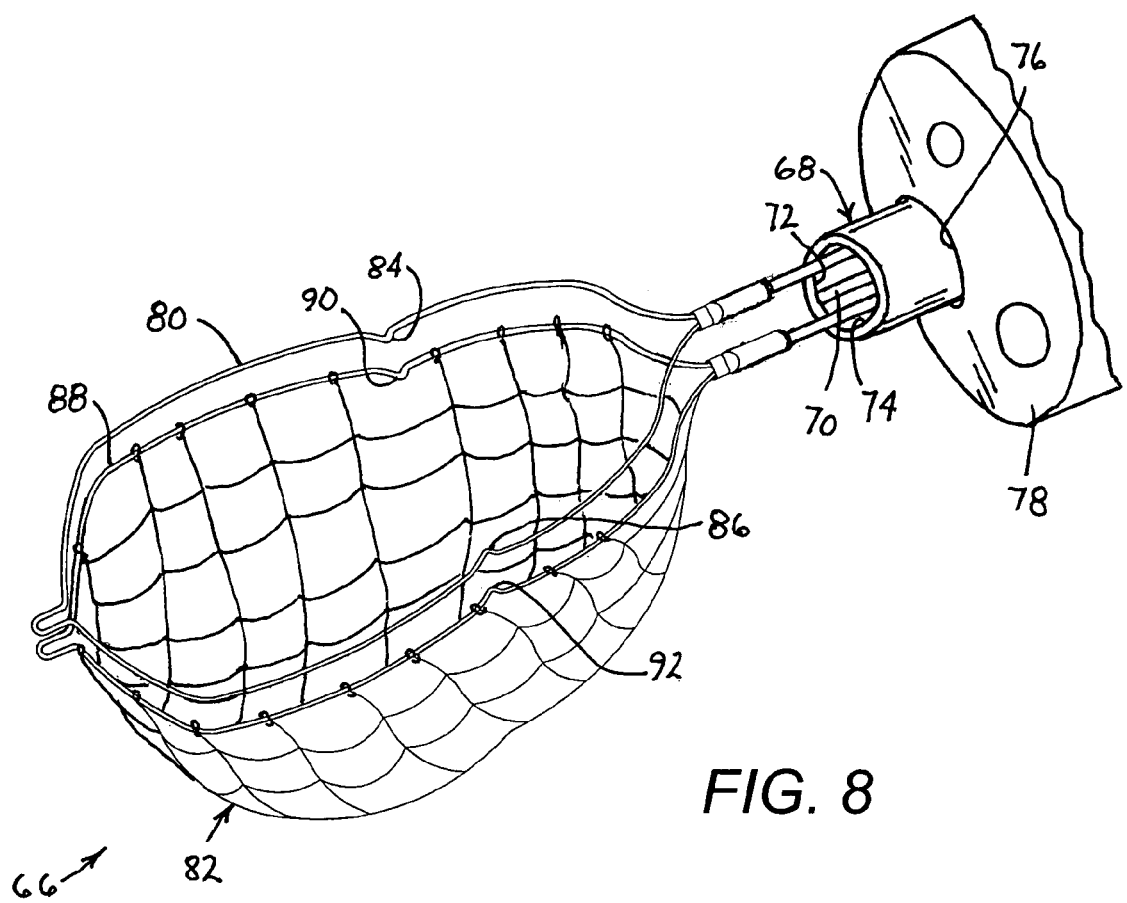
FIG. 8 is a schematic perspective view of a dual lumen endoscopic instrument including a cauterization snare and a retrieval basket or pouch each having a form in accordance with the present invention.

As depicted in FIG. 8, an endoscopic instrument assembly 66 includes a catheter 68 having a longitudinal partition 70 forming two parallel lumens 72 and 74. Catheter 68 is passed through the biopsy channel 76 of a flexible endoscope 78. A cauterization loop 80 as discussed hereinabove with references to FIGS. 1-5 is inserted through lumen 72, while a non-electrified retrieval basket 82 as discussed hereinabove with reference to FIGS. 6 and 7, is inserted through lumen 74. Cauterization loop 80 is formed with a pair of inwardly pointing notches or dents 84 and 86, while a loop 88 of retrieval basket 82 is provided with two inwardly pointing notches or dents 90 and 92. Notches or dents 84 and 86 facilitate the use of cauterization loop 80 to sever polyps of different sizes, while notches or dents 90 and 92 facilitate the use of retrieval basket 82 to capture differently dimensioned tissue masses, as discussed in detail above. The structure and utilization of dual lumen snare and retrieval devices is discussed in U.S. Pat. No. 5,759,187.

Figures 9, 10:
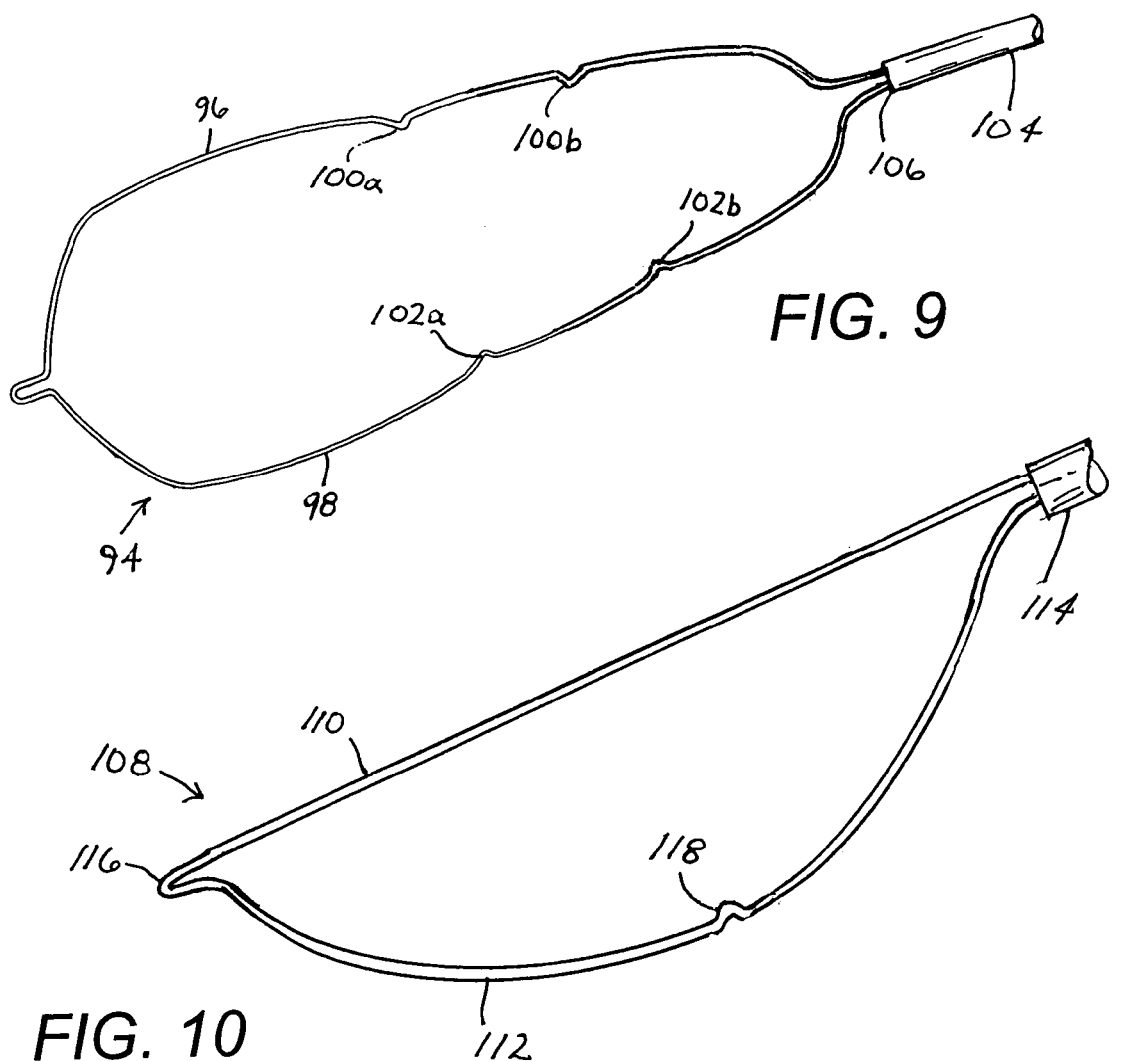
FIG. 9 is a schematic partial perspective view of another medical tissue retrieval device in accordance with the present invention.
FIG. 10 is a schematic partial perspective view of yet another medical tissue retrieval device in accordance with the present invention.

FIG. 9 depicts a loop 94 that may be used as a cauterization loop or as a carrier for a retrieval pouch. Loop 94 is similar to that shown in FIGS. 1-5, except for the inclusion of additional notches or dents. Loop 94 includes two generally longitudinal loop sections 96 and 98 each provided with a plurality of spaced notches or dents 100$a$, 100$b$ and 102$a$, 102$b$, respectively. As an extension of principles explicated hereinabove with reference to FIGS. 1-5, loop 94 is alternatively utilizable in three different sizes. A largest size is shown in FIG. 9. After a partial withdrawal of loop 94 into a tubular member 104 so that notches or dents 100$b$ and 102$b$ are located at a mouth or distal end 106 of tubular member 104, loop 94 is utilizable in a medium-size configuration. After a further withdrawal of loop 94 into tubular member 10 so that notches or dents 100$a$ and 102$a$ are located at the mouth 106 of the tubular member produces a smallest effective size of the loop.

FIG. 9 demonstrates that an increasing number of notches or dents may be formed along a medical loop to provide the loop with an increasing number of effective size options. FIG. 10 demonstrates that one or more notches or dents as disclosed herein may be provided in loops of different shapes.

As shown in FIG. 10, a loop 108 has a first section 110 that is linear and a second section 112 that is bowed. Loop 108 thus assumes a D shape. In an expanded or freed configuration of loop 108, loop sections 110 and 112 extend between a distal end of a tubular member 114 and a nose 116 of the loop. Bowed or arced section 112 is provided with at least one notch or dent 118 as described above with reference to FIGS. 1-5. Loop 108 is of particular use in certain cases, for instance, where a polyp stands in close proximity to a colon wall.

Loops 94 and 108 may be provided with pouches (not shown) to form retrieval baskets.

Basically, any shape of snare, be it hexagonal, round, or any other shape can be divided into two or more snares by proper application or placement of notches as described herein. Some may require differently angled notches, for example, deeper and more prominent notches, depending on the original shape of the snare.

Although the invention has been described in terms of particular embodiments and applications, one of ordinary skill in the art, in light of this teaching, can generate additional embodiments and modifications without departing from the spirit of or exceeding the scope of the claimed invention. For example, in some applications, it may be effective to provide only one of the loop sections 28 and 30 with a notch or dent. Accordingly, it is to be understood that the drawings and descriptions herein are proffered by way of example to facilitate comprehension of the invention and should not be construed to limit the scope thereof.

What is claimed is:

1. A medical cauterization snare instrument comprising:
a tubular member;
an elongate member disposed at least partially inside said tubular member;
a resilient loop having a substantially planar fully expanded configuration of a first size attached to one end of said elongate member, said loop including a first bend on a side of said loop opposite said elongate member, said loop further including two loop sections each extending from said elongate member to said bend, at least one of said loop sections being formed with at least one notch or dent for enabling a use of said loop in at least one second size smaller than said first size upon a positioning of said loop by moving said elongate member and said tubular member relative to one another so that said notch or dent is disposed at a mouth opening of said tubular member, said two loop sections being disposed entirely outside of said tubular member in said fully expanded configuration of said loop, said one of said loop sections including, in the fully expanded configuration of said loop, a second bend or kink disposed between said first bend and said notch or dent, said second bend or kink defining a concavity facing towards the other of said loop sections, said loop being made of an electrically conductive material for cauterizing organic tissues of a patient, said notch or dent being so small relative to said loop that said loop in the fully expanded configuration takes the form of a single oval having a width that is substantially unaffected by said notch or dent so that said loop in the fully expanded configuration can be used to sever a polyp substantially larger than any polyp severable by said second size of said loop;
a connector electrically linked to said loop for operatively coupling said loop to a voltage source; and
wherein each of said notches or dents includes a pair of linear segments connected to one another by an arcuate bight, said segments being disposed at an angle of approximately 80° to approximately 120° relative to one another.

2. The instrument defined in claim 1 wherein each of said loop sections is formed with a respective notch or dent for enabling use of said loop in said second size upon a positioning of said loop relative to said tubular member so that the notches or dents are disposed at said mouth opening of said tubular member, said notches or dents both being so small relative to said loop that said loop in the fully expanded configuration takes the form of a single oval having a width that is substantially unaffected by said notches or dents so that said loop in the fully expanded configuration can be used to sever a polyp substantially larger than any polyp severable by said second size of said loop.

3. The instrument defined in claim 2 wherein the notches or dents are disposed at substantially the same first distance from said one end of said elongate member and substantially the same second distance from said first bend.

4. The instrument defined in claim 3 wherein said first distance is approximately 30% to approximately 40% of the sum of said first distance and said second distance.

5. The instrument defined in claim 4 wherein said first bend is part of a nose projection of said loop, each of said loop sections including a respective second bend or kink disposed between said nose projection and the respective one of said notches or dents.

6. The instrument defined in claim 5 wherein the respective second bends or kinks in said loop sections are located at approximately the same distance from said nose projection so that said loop is provided with an enlarged distal end portion.

7. The instrument defined in claim 2 wherein the notch or dent of each one of said loop sections extends toward the other loop section.

8. The instrument defined in claim 2 wherein said loop in said planar configuration lies in a single plane, said notches or dents being located in said plane.

9. The instrument defined in claim 2 wherein said loop has a relaxed configuration wherein said loop sections are spaced from one another by a loop width, each of said notches or dents having a width dimension measured in a direction from the respective loop section towards the other loop section, said width dimension being no larger than approximately fifteen percent of said loop width.

10. The instrument defined in claim 2 wherein said notches or dents each have a V shape.

11. The instrument defined in claim 1, further comprising a pouch slidably attached to said loop.

12. The instrument defined in claim 1 wherein said one of said loop sections is curved in a fully expanded configuration of said loop, the other of said loop sections being straight in said fully expanded configuration of said loop.

13. The instrument defined in claim 1 wherein said notch or dent is one of a plurality of notches or dents formed along said one of said loop sections, said notches or dents being so small relative to said loop that said loop in the fully expanded configuration takes the form of a single oval having a width that is substantially unaffected by said notches or dents so that said loop in the fully expanded configuration can be used to sever a polyp substantially larger than any polyp severable by said second size of said loop.

14. The instrument defined in claim 1 wherein said notch or dent is located at a first distance from said one end of said elongate member and a second distance from said first bend, said first distance being approximately 30% to approximately 40% of the sum of said first distance and said second distance.

15. The instrument defined in claim 1 wherein said loop in said planar configuration lies in a single plane, said notch or dent being located in said plane.

16. The instrument defined in claim 1 wherein said loop has a relaxed configuration wherein said loop sections are spaced from one another by a loop width, said notch or dent having a width dimension measured in a direction from said one of said loop sections towards the other of said loop sections, said width dimension being no larger than approximately fifteen percent of said loop width.

17. The instrument defined in claim 1 wherein said notch or dent has a V shape.

18. The instrument defined in claim 1 further comprising a pouch attached to said loop, said loop defining a mouth opening of said pouch.

19. A medical cauterization snare instrument comprising:
a tubular member;
an elongate member disposed at least partially inside said tubular member;
a resilient loop of a first size attached to one end of said elongate member, said loop including a first bend on a side of said loop opposite said elongate member, said loop further including two loop sections each extending from said elongate member to said bend, at least one of said loop sections being formed with at least one notch or dent for enabling a use of said loop in at least one second size smaller than said first size upon a positioning of said loop by moving said elongate member and said tubular member relative to one another so that said notch or dent is disposed at a mouth opening of said tubular member, the notch or dent in said one of said loop sections extending toward the other loop section, said loop having a fully opened relaxed configuration wherein both said loop sections are disposed outside of said tubular member, said one of said loop sections including, in said fully expanded configuration of said loop, a second bend or kink disposed between said first bend and said notch or dent, said second bend or kink defining a concavity facing towards the other of said loop sections, said notch or dent being so small relative to said loop that said loop in the fully opened relaxed configuration takes the form of a single oval having a width that is substantially unaffected by said notch or dent so that said loop in the fully opened relaxed configuration can be used to sever a polyp substantially larger than any polyp severable by said second size of said loop, said loop being made of an electrically conductive material for cauterizing organic tissues of a patient;

a connector electrically linked to said loop for operatively coupling said loop to a voltage source; and wherein each of said notches or dents includes a pair of linear segments connected to one another by an arcuate bight, said segments being disposed at an angle of approximately 80° to approximately 120° relative to one another.

20. The instrument defined in claim 19 wherein each of said loop sections is formed with at least one respective notch or dent for enabling use of said loop in said second size upon a positioning of said loop relative to said tubular member so that the notches or dents are disposed at said mouth opening of said tubular member, each notch or dent in each of said loops sections extending toward the other loop section, each of said loop sections including, in said fully expanded configuration of said loop, a second bend or kink disposed between said first bend and the respective notch or dent and defining a concavity facing towards the other of said loop sections, said notches or dents being so small relative to said loop that said loop in the fully expanded configuration takes the form of a single oval having a width that is substantially unaffected by said notches or dents so that said loop in the fully expanded configuration can be used to sever a polyp substantially larger than any polyp severable by said second size of said loop.

21. The instrument defined in claim 19 wherein said loop has a relaxed configuration wherein said loop sections are spaced from one another by a loop width, said notch or dent having a width dimension measured in a direction from said one of said loop sections towards the other loop section, said width dimension being no larger than approximately fifteen percent of said loop width.

22. The instrument defined in claim 19 wherein said one of said loop sections is curved in a fully expanded configuration of said loop, the other of said loop sections being straight in said fully expanded configuration of said loop.

23. The instrument defined in claim 19 wherein said notch or dent is one of a plurality of notches or dents formed along said one of said loop sections, said notches or dents being so small relative to said loop that said loop in the fully expanded configuration takes the form of a single oval having a width that is substantially unaffected by said notches or dents so that said loop in the fully expanded configuration can be used to sever a polyp substantially larger than any polyp severable by said second size of said loop.

24. The instrument defined in claim 19 wherein said loop lies in a single plane, said notch or dent being located in said plane.

25. The instrument defined in claim 19 wherein said loop has a relaxed configuration wherein said loop sections are spaced from one another by a loop width, said notch or dent having a width dimension measured in a direction from said one of said loop sections towards the other of said loop sections, said width dimension being no larger than approximately fifteen percent of said loop width.

26. A medical cauterization snare instrument comprising:

a tubular member;

an elongate member disposed at least partially inside said tubular member;

a resilient loop of a first size attached to one end of said elongate member, said loop including a first bend on a side of said loop opposite said elongate member, said loop further including two loop sections each extending from said elongate member to said bend, at least one of said loop sections being formed with at least one indentation or dimple for enabling a use of said loop in at least one second size smaller than said first size upon a positioning of said loop by moving said elongate member and said tubular member relative to one another so that said indentation or dimple is disposed at a mouth opening of said tubular member, said two loop sections being disposed entirely outside of said tubular member in said fully expanded configuration of said loop, said one of said loop sections including, in the fully expanded configuration of said loop, a second bend or kink disposed between said first bend and said indentation or dimple, said second bend or kink defining a concavity facing towards the other of said loop sections, said indentation or dimple being so small relative to said loop that said loop in the fully opened relaxed configuration takes the form of a single oval having a width that is substantially unaffected by said indentation or dimple so that said loop in the fully opened relaxed configuration can be used to sever a polyp substantially larger than any polyp severable by said second size of said loop, said loop being made of an electrically conductive material for cauterizing organic tissues of a patient;

a connector electrically linked to said loop for operatively coupling said loop to a voltage source; and wherein each of said notches or dents includes a pair of linear segments connected to one another by an arcuate bight, said segments being disposed at an angle of approximately 80° to approximately 120° relative to one another.

27. The instrument defined in claim 26 wherein said indentation or dimple comprises at least three mutually proximate bends in said one of said loop sections, said mutually proximate bends being substantially closer to each other than to any other bend in said loop.

28. The instrument defined in claim 26 wherein said indentation or dimple faces an inside of said loop.

29. The instrument defined in claim 26 wherein said loop substantially lies in a single plane, said indentation or dimple being disposed in said plane.

30. A medical cauterization method comprising:

(a) providing a cauterization snare instrument including:

a tubular member;

an elongate member disposed at least partially inside said tubular member;

a resilient loop having a substantially planar fully expanded configuration of a first size attached to one end of said elongate member, said loop including a first bend on a side of said loop opposite said elongate member, said loop further including two loop sections each extending from said elongate member to said bend, at least one of said loop sections being formed with at least one notch or dent for enabling a use of said loop in at least one second size smaller than said first size upon a positioning of said loop by moving said elongate member and said tubular member relative to one another so that said notch or dent is disposed at a mouth opening of said tubular member, said two loop sections being disposed entirely outside of said tubular member in said fully expanded configuration of said loop, said one of said loop sections including, in the fully expanded configuration of said loop, a second bend or kink disposed between said first bend and said notch or dent, said second bend or kink defining a concavity facing towards the other of said loop sections, said loop being made of an electrically conductive material for cauterizing organic tissues of a patient, said notch or dent being so small relative to said loop that said loop in the fully expanded configuration takes the form of a single oval having a width that is substantially unaffected by said notch or dent so that said loop in the fully expanded configuration can be used to sever a polyp substantially larger than any polyp severable by said second size of said loop; and a connector electrically linked to said loop for operatively coupling said loop to a voltage source; and wherein each of said notches or dents includes a pair of linear segments connected to one another by an arcuate bight, said segments being disposed at an angle of approximately 80° to approximately 120° relative to one another;

(b) inserting a distal end portion of said tubular member into a patient, said loop being disposed inside said tubular member during the inserting of said distal end portion;

(c) thereafter ejecting said loop from said tubular member inside the patient; (d) expanding said loop to said fully expanded configuration;

(e) placing the fully expanded loop over a first polyp;

(f) thereafter withdrawing said loop in a proximal direction and thereby closing said loop about said polyp;

(g) during the closing of said loop, conducting current through said loop to sever the polyp about a base region thereof, and alternatively to steps (d)-(g):

(h) expanding said loop to said second size;

(i) placing the loop expanded to said second size over a second polyp, said first polyp being larger than said second polyp;

(j) thereafter withdrawing said loop in a proximal direction and thereby closing said loop about said second polyp; and (k) during the closing of said loop about said second polyp, conducting current through said loop to sever the second polyp about a base region thereof.

31. The method defined in claim 30 wherein each of said loop sections is formed with a respective notch or dent for enabling use of said loop in said second size upon a positioning of said loop relative to said tubular member so that said notches or dents are disposed at said mouth opening of said tubular member.

* * * * *